(12) United States Patent
Kim et al.

(10) Patent No.: US 11,529,628 B2
(45) Date of Patent: Dec. 20, 2022

(54) AUTOMATED IMMUNOASSAY DEVICE AND METHOD USING LARGE MAGNETIC PARTICLE COMPLEX

(71) Applicant: EzDia Tech Inc., Cheonan-si (KR)

(72) Inventors: Joo-ho Kim, Cheonan-si (KR); Mun-tak Son, Cheonan-si (KR)

(73) Assignee: EZDIA TECH INC., Cheonan-si (KR)

( * ) Notice: Subject to any disclaimer, the term of this patent is extended or adjusted under 35 U.S.C. 154(b) by 551 days.

(21) Appl. No.: 16/609,115

(22) PCT Filed: Apr. 27, 2018

(86) PCT No.: PCT/KR2018/004936
§ 371 (c)(1),
(2) Date: Oct. 28, 2019

(87) PCT Pub. No.: WO2018/199689
PCT Pub. Date: Nov. 1, 2018

(65) Prior Publication Data
US 2021/0101144 A1  Apr. 8, 2021

(30) Foreign Application Priority Data

Apr. 28, 2017 (KR) .......... 10-2017-0055480

(51) Int. Cl.
*B01L 3/00* (2006.01)
*B01L 3/02* (2006.01)
(Continued)

(52) U.S. Cl.
CPC ....... *B01L 3/502715* (2013.01); *B01L 3/0289* (2013.01); *G01N 33/54326* (2013.01);
(Continued)

(58) Field of Classification Search
None
See application file for complete search history.

(56) References Cited

U.S. PATENT DOCUMENTS

2013/0331298 A1   12/2013   Rea

FOREIGN PATENT DOCUMENTS

EP    1130397    *  9/2001
JP    4531698       8/2010
(Continued)

OTHER PUBLICATIONS

International Search Report for International Application No. PCT/KR2018/004936, dated Feb. 8, 2019.

*Primary Examiner* — Rebecca M Giere
(74) *Attorney, Agent, or Firm* — Kile Park Reed & Houtteman PLLC (57) ABSTRACT

The present invention relates to an immunoassay apparatus and a method thereof. The immunoassay apparatus including a cartridge 13 in which a tube for T tip 9, a reaction tube 11, a tube for washing 3, and a tube for signal measurement 5 are integrally coupled or individually configured; a T tip 7 and a magnetic rod 31 used for performing reaction and washing processes while moving large magnetic particles m, capture materials, signal materials, and analyte materials with magnetic force by entering successively a plurality of tubes 3 and 5; a cartridge holder 15 in which the cartridge 13 is seated; and a heating member 17 that generates heat by being disposed at a region in which the reaction tube 11 is seated in the cartridge holder 15; is configured in a state where each of the different shapes of magnetic particles is bound with materials.

5 Claims, 7 Drawing Sheets (a)　(b)　(c)

(51) Int. Cl.
*G01N 33/543* (2006.01)
*G01N 35/00* (2006.01)

(52) U.S. Cl.
CPC .. *G01N 35/0098* (2013.01); *B01L 2200/0657* (2013.01); *B01L 2200/0668* (2013.01); *B01L 2300/087* (2013.01); *B01L 2400/043* (2013.01)

(56) References Cited

FOREIGN PATENT DOCUMENTS

| | | |
|---|---|---|
| KR | 10-2002-7001752 | 3/2002 |
| KR | 10-2011-0106892 | 9/2011 |
| KR | 10-2013-0107146 | 10/2013 |
| KR | 10-2015-0038155 | 4/2015 |
| KR | 10-2016-0000001 | 1/2016 |

* cited by examiner

AUTOMATED IMMUNOASSAY DEVICE AND METHOD USING LARGE MAGNETIC PARTICLE COMPLEX

TECHNICAL FIELD

The present invention relates to an automatic immunoassay device and a method thereof, more specifically, a technology to provide the immunoassay device and a method thereof for automatically performing a process of extracting and discharging large magnetic particles of various shapes by a simple method using a magnetic rod and a T tip, a washing process for increasing the accuracy of immune response results using the large magnetic particles in one cartridge, and multiple inspections on the large magnetic particles of the various shapes at once through image analysis in one tube, by improving a structure.

BACKGROUND ART

Recently, as a human genome project is completed and a post genome era arrives, a large amount of micro information is produced, which is difficult to process quickly in a related laboratory analysis system.

According to such trend, biological detection systems for the identification of life phenomena and for the development and diagnosis of new drugs are developed in a form of point-of-care testing to analyze samples quickly and accurately in a small amount.

Since most of the biochemical samples to be analyzed are in solution, a technology capable of operating automatically and quickly sample reaction-specific cartridges and such cartridges in order to be able to inspect liquid samples on-site and see results, is the most important factor.

A cartridge structure and an automatic inspection system are the elements that enable this inspection, and the core technologies that are the basis for the commercialization of a field inspection technology.

The field inspection technology is a system that comprehensively implements chemical and biological experiments and analyses that undergo a plurality of experimental steps and reactions on one cartridge existing on one bench. This field inspection system is configured with a sampling region, inspection reaction, cleaning, a detector, and a controller for controlling them.

Implementation of the field inspection system capable of quickly performing analysis on rapidly increasing bioinformation may be effectively accomplished by binding with appropriate bioassay methods.

A method for analyzing biomolecules includes immunoassay, DNA hybridization, and receptor-based analysis. A detection method for analyzing these biomolecules is widely used not only in a laboratory but also in medical diagnosis and drug development.

An immunoassay method as an analysis technology using antigen-antibody binding reaction includes various forms depending on test principle, and DNA hybridization analysis uses complementary binding between probe DNA and target DNA.

The receptor-based assay is also an analysis method using binding capacity between a specific molecule and its receptor. As described above, the selective binding ability on detection molecules of the antibody, DNA, RNA, and molecular receptors capable of specific binding may be used to detect various biomolecules.

Since a binding process of these biomolecules cannot be directly observed, a labeling material capable of generating a measurable signal is used.

In general, fluorescent materials, radioactive materials, enzymes, magnetic particles or the like are used as the labeling material. In such a measurement method, it is important to generate a high sensitivity signal so that a very small amount of detection molecules may be recognized.

In particular, recently, by the development of synthetic chemistry and life science, target materials to be analyzed are diversified in fields of new drug development, diagnosis, and the like. In addition, since these target materials are very expensive and not easily available, the need for cost reduction through trace analysis is increasing. As one of detection methods for ensuring high sensitivity signal generation, various methods using the magnetic particles are reported.

However, the analysis methods of the related art have difficulty in effectively extracting or discharging the labeling materials such as magnetic particles in wells.

In addition, the related analysis methods have a problem in that only one magnetic particle may be inspected at a time, which takes a long time and makes the inspection complicated.

SUMMARY OF INVENTION

Technical Problem

Therefore, the present invention is to provide an immunoassay apparatus and a method thereof for automatically performing a process of extracting and discharging large magnetic particles of various shapes by a simple method using a magnetic rod and a T tip, and a washing process for increasing the accuracy of immune response results using the large magnetic particles in one cartridge, by improving a structure.

In addition, the present invention is to provide the immunoassay apparatus and the method thereof for automatically performing multiple inspections on the large magnetic particles of the various shapes at once through image analysis in one tube.

Solution to Problem

In order to realize the above object of the present invention, an immunoassay apparatus according to an embodiment of the present invention includes a cartridge 13 in which a tube for T tip 9, a reaction tube 11, a tube for washing 3, and a tube for signal measurement 5 are integrally coupled or individually configured; a T tip 7 and a magnetic rod 31 used for performing reaction and washing processes while moving large magnetic particles m, capture materials, signal materials, and analyte materials with magnetic force by entering successively a plurality of tubes 3 and 5; a cartridge holder 15 in which the cartridge 13 is seated; a heating member 17 that generates heat by being disposed at a region in which the reaction tube 11 is seated in the cartridge holder 15; and an image analyzer 14 capable of performing multiple inspections by recognizing each of the analyte materials depending on shapes by analyzing the magnetic particles of various shapes as images.

An analysis method according to another embodiment of the present invention includes a first step S100 of injecting a certain amount of a sample into the reaction tube 11 of the cartridge 13, inserting the T tip 7 into a tube for T tip, and then seating the cartridge 13 in the cartridge holder 15; a second step S110 of proceeding the reaction by heating the reaction tube 11 to generate predetermined temperature by applying power to the heating member 17; a third step S120 of inserting the T tip 7 into the reaction tube 11 by a pick-up machine, and attaching the magnetic particles m on the outer surface of the T tip 7 due to the magnetic force of a magnet rod 31, after proceeding the reaction; a fourth step S130 of performing washing by up and down reciprocating movement after moving to a washing tube in a state where the magnetic particles m are attached to the outside of the T tip; a fifth step S140 of discharging the magnetic particles m to the tube for signal measurement 5 by raising the magnetic rod 31 from the T tip 7 after moving the T tip 7 to the tube for signal measurement 5; and a sixth step S150 of capturing and separating only specific analyte materials per the magnetic particles of one shape or various shapes by analyzing the discharged large magnetic particles m as images by an image analyzer.

Advantageous Effects of Invention

An immunoassay apparatus according to an embodiment of the present invention has following advantages.

First, a plurality of tubes in which magnetic particles, capture materials, signal materials, and analyte materials are stored, extracted, and discharged, are integrally coupled to form a single cartridge, and the cartridge is seated on a cartridge holder in which a heating member is disposed. By doing so, there is an advantage that immunoassay may be performed quickly and easily.

Second, since the magnetic particles are attached to the outer circumferential surface of the tip if necessary by disposing a magnetic rod to be inserted into a tip and washing is performed in a state where the magnetic particles are discharged by separating the magnetic rod from the tip, there is an advantage that more efficient cleaning may be achieved.

Third, by maintaining a distance between a reaction tube and a T-tip tube and a distance between the reaction tube and a cleaning tube by a distance longer than the thickness of the heating member, there is an advantage that it is possible to prevent the heat of the heating member from being transferred to the tube other than the reaction tube.

Fourth, since the magnetic particles are basically bound with materials capable of capturing analyte materials and configured with the magnetic particles of one shape or various shapes, there is an advantage that multiple inspections may be performed simultaneously by capturing specific analyte materials per different shapes of the magnetic particles.

Fifth, by configuring the cartridge by integrally coupling the plurality of tubes each other or configuring individually, it is possible to variously implement structural design of the cartridge.

DESCRIPTION OF EMBODIMENTS

Hereinafter, an immunoassay apparatus according to an embodiment of the present invention will be described in detail with reference to the drawings.

As illustrated in FIG. 1 to FIG. 6, a cartridge system 1 of the present invention is applied to an immunoassay apparatus, includes a plurality of tubes 3 and 5 in which each of large magnetic particles m of various shapes, capture materials, signal material, and analyte materials is stored, and a system 1 for analyzing immunity by repeating processes of entering successively a T tip 7 into the plurality of tubes 3 and 5, and capturing the magnetic particles m.

Figure 1:
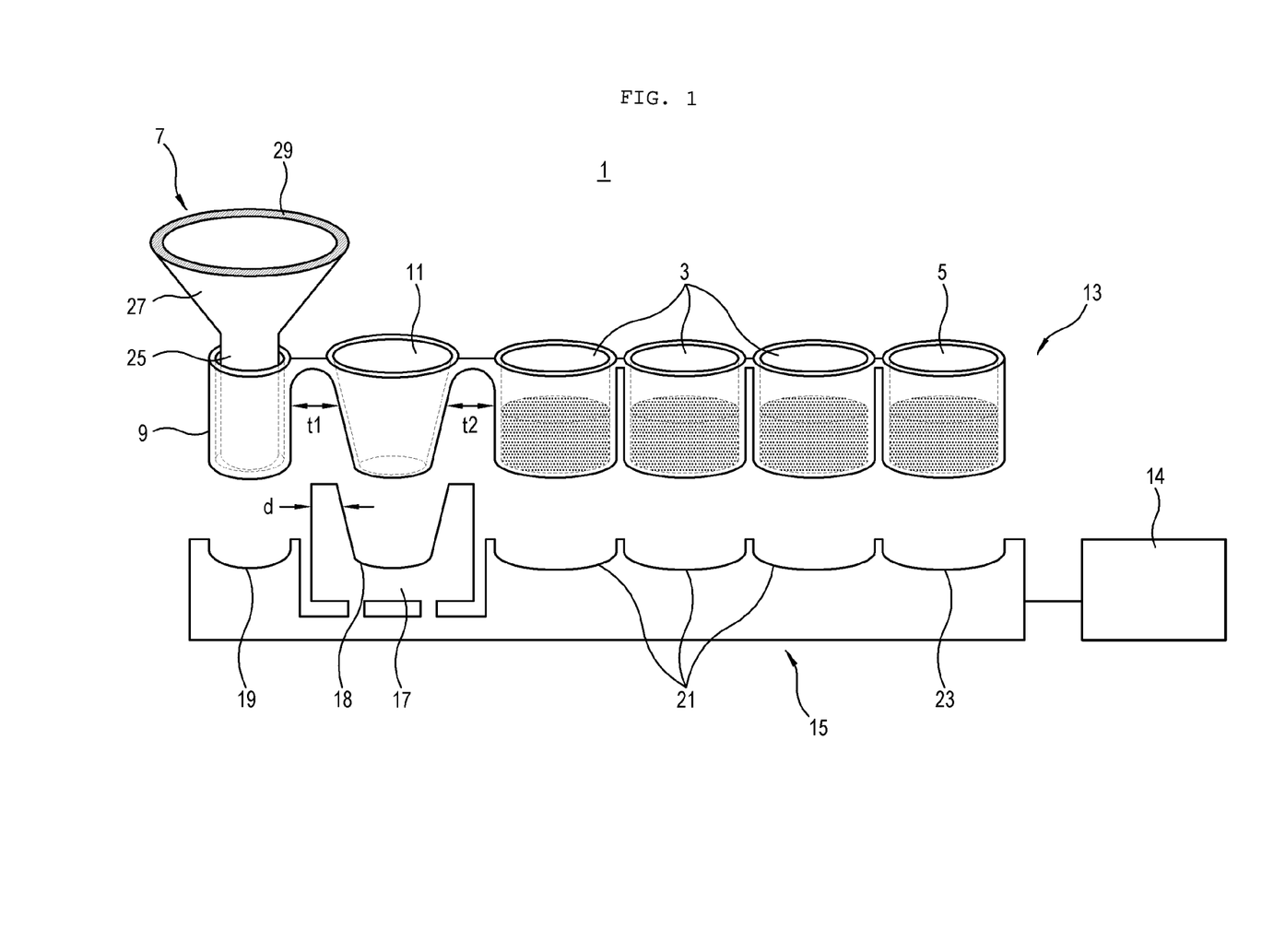
FIG. 1 is a diagram illustrating a cartridge in which a tube for T tip, a reaction tube, tubes for washing, and a tube for signal measurement are integrally coupled, a T tip, and a cartridge holder, as an embodiment of the present invention.

The cartridge system 1 includes a cartridge 13 including a tube for T tip 9, a reaction tube 11, tubes for washing 3, and a tube for signal measurement 5; a T tip 7 and a magnetic rod 31 used for performing reaction and washing processes while moving the large magnetic particles m of various shapes, the capture materials, the signal materials, and the analyte materials with magnetic force by entering successively the plurality of tubes 3 and 5; a cartridge holder 15 in which the cartridge 13 is seated; a heating member 17 that generates heat by being disposed at a region in which the reaction tube 11 is seated in the cartridge holder 15; and an image analyzer 14 capable of performing multiple inspections by recognizing each of analyte materials depending on shapes by analyzing the magnetic particles of various shapes as images.

Figure 3:
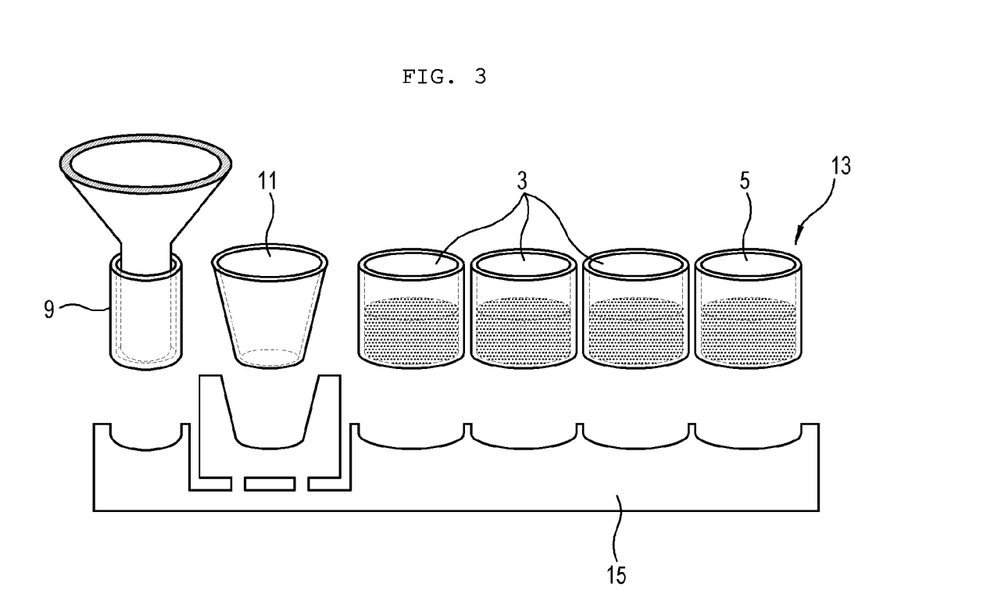
FIG. 3 is a diagram illustrating a cartridge in which each tube is individually configured as another embodiment of the cartridge illustrated in FIG. 1.

In the cartridge system 1 having such structure, the cartridge 13 is configured with a plurality of tubes 9, 11, 3, and 5 such that each of the large magnetic particles m of various shapes, the capture materials, the signal materials, and the analyte materials is stored therein, and is reacted and washed. At this time, the plurality of tubes 9, 11, 3, and 5 may be integrally coupled with each other as illustrated in FIG. 1, and each of the plurality of tubes 9, 11, 3, and 5 may be configured independently as illustrated in FIG. 3.

For example, the cartridge 13 has a structure in which the tube for T tip 9, the reaction tube 11, the tubes for washing 3, and the tube for signal measurement 5 are arranged in one row.

In this manner, by coupling the plurality of tubes 9, 11, 3, and 5 integrally or configuring individually, a structure of the cartridge may be variously selected according to the analysis target.

Of course, a tube other than the above-described tube may be further arranged.

At this time, since the reaction tube 11 is seated on the heating member 17 disposed on the cartridge holder 15 and heating reaction proceeds, heat may be transferred to neighboring tube for T tip 9 and tubes for washing 3.

Therefore, it is preferable that a distance t1 between the reaction tube 11 and the tube for T tip 9 and a distance t2 between the reaction tube 11 and a washing tube 3 are separated by a predetermined distance to prevent transfer of excessive heat. That is, it is preferable that these distances t1 and t2 are maintained longer than the thickness d of the heating member 17, or longer than a distance between a plurality of the tubes for washing 3.

In addition, the reaction tube 11 has a structure with a wide upper and a narrow lower in which a length of the lower diameter is smaller than that of the upper diameter such that the heat transferred from the lower heating member 17 may be more effectively transferred to promote the reaction.

The T tip 7 may be placed in the tube for T tip 9, the magnetic particles m may be stored in the reaction tube 11, washing liquid may be stored in the tubes for washing 3, and signal analysis liquid may be stored in the tube for signal measurement 5.

Of course, the arrangement of the plurality of tubes may be appropriately modified depending on the immunoassay environment.

Figure 2:
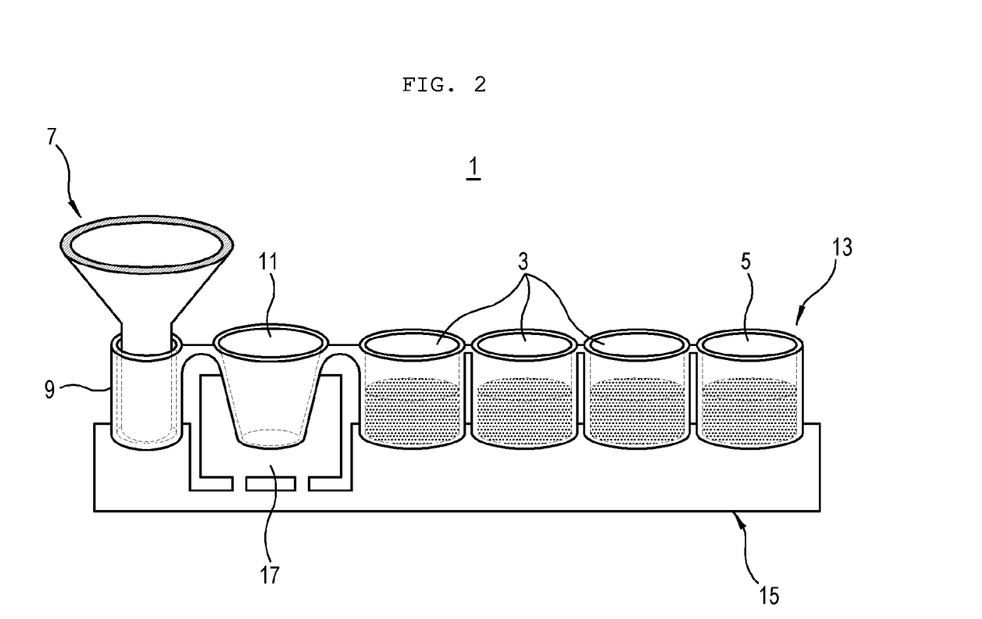
FIG. 2 is a diagram illustrating a state in which the cartridge illustrated in FIG. 1 is coupled in the cartridge holder.

As described above, the cartridge 13 configured with the plurality of tubes 3 and 5 may be stably supported by being seated in the cartridge holder 15.

The lower portion of the cartridge holder 15 is level, and a plurality of mounting stages 19, 21, and 23 in which each tube may be seated and the heating member 17 are arranged on the upper portion thereof.

That is, the cartridge holder 15 includes a first mounting stage 19 in which the tube for T tip 9 is seated; the heating member 17 in which the reaction tube 11 is seated and heated; a second mounting stage 21 in which the tubes for washing 3 are seated; and a third mounting stage 23 in which the tube for signal measurement 5 is seated.

The plurality of mounting stages 19, 21, and 23, and the heating member 17 may be concave so that the tubes may be stably coupled.

In addition, since the heating member 17 generates proper heat by a heating coil, a heat generation element or the like, reaction may be activated by heating the reaction tube 11.

Therefore, the reaction tube 11 may be seated inside a holder 18 formed on the upper portion of the heating member 17.

Meanwhile, the T tip 7 has a structure in which a cylinder pipe 25 is formed in the lower portion and an induction pipe 27 of an inverted triangle is formed in the upper portion. Therefore, in a case where the magnetic rod 31 enters from the upper portion to the inside of the T tip 7, the magnetic rod may be smoothly entered along the inclined surface of the induction pipe 27.

The magnetic rod 31 is entered inside the T tip 7, and the magnetic force of the magnetic rod 31 forms a magnetic field that reaches within an outside constant distance of the T tip 7 after the entering.

At this time, since the magnetic rod 31 is the magnetic materials, the T tip 7 is formed with non-magnetic materials.

Therefore, in a case where the T tip 7 enters the inside of the tube in which the magnetic materials are stored, the magnetic materials are adhered to the outer surface of the T tip 7 by the magnetic force.

On the contrary, in a case where the magnetic rod 31 is separated from the T tip 7, since the magnetic force around the T tip 7 is extinguished, the attached magnetic materials may be separated from the T tip 7.

As a result, after the T tip 7 into which the magnetic rod 31 is inserted enters the tube in which the magnetic materials are stored, the magnetic materials may be separated in a case where the magnetic rod 31 is removed by absorbing on the surface and moving to another tube in this state.

At this time, the magnetic particles are in a state where a material (for example, antibody) in which the magnetic particles capable of capturing basically the analyte materials is bound thereto, and configured with the magnetic particles of one shape or various shapes.

Since it is configured that each of the different shapes of magnetic particles is bound with materials (for example, antibody) capable of capturing only specific analyte materials, if the analyte materials are present in a sample, the analyte materials are captured in the magnetic particles and the signal materials (for example, another antibody with fluorescent material) are bound with the analyte materials captured in the magnetic particles such that magnetic material-analyte material-signal material composites are formed.

After the reaction, a magnetic composite, sample impurity that does not react with the magnetic material, and a signal material remaining without the reaction are present together in the reaction tube.

Figure 7:
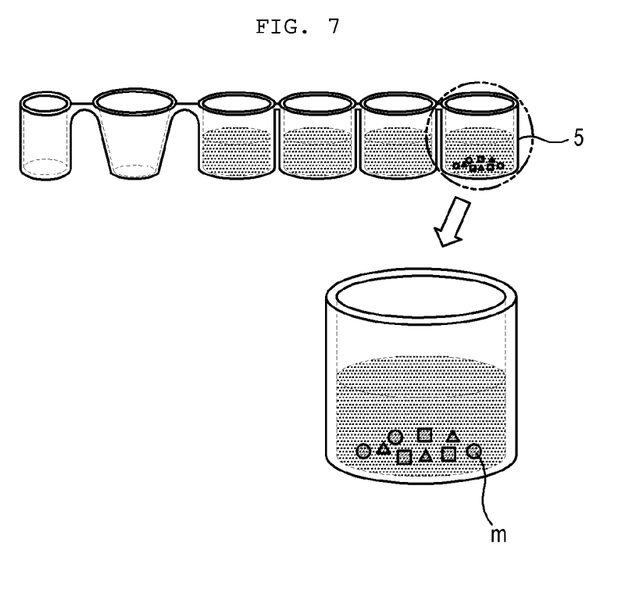
FIG. 7 illustrates various large magnetic particle composites put down in the tube for signal measurement after removing the T tip, and is a diagram illustrating that multiple scanning may be performed in one tube by recognizing it as a result of different analyte materials depending on shapes by analyzing shapes of the large magnetic particles as images.

The discharged large magnetic particles m and the magnetic particles composite are analyzed as images by the image analyzer 14 and only specific analyte materials per the magnetic particles of one shape or various shapes are captured and separated such that the multiple inspections may be performed simultaneously.

That is, as illustrated in FIG. 7, the magnetic particles m and the magnetic particle composite in a state of being discharged and sunk in the tube for signal measurement 5 may be distinguished in shapes by using the image analyzer 14 according to their shapes.

That is, since a result obtained by analyzing and imaging the shape of the large magnetic particles with the image analyzer 14, may be recognized as the result of each different analyte materials according to each shape, multiple scanning may be simultaneously performed in one tube.

At this time, as the image analyzer 14, various analyzers may be used.

Figure 8:
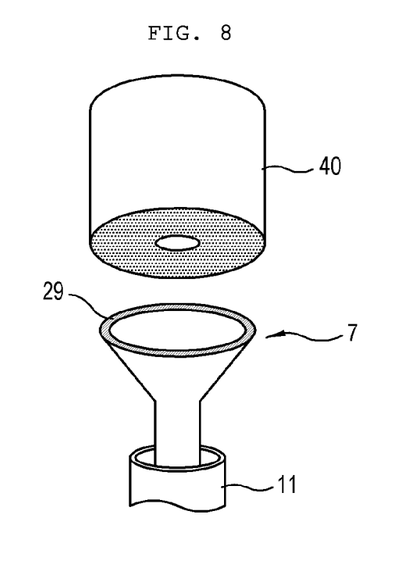
FIG. 8 is a diagram illustrating an elevator that moves the T tip up and down by picking up the T tip illustrated in FIG. 1.

A circular magnetic plate 29 may be mounted on the upper edge of the induction pipe 27 of the T tip 7. That is, as illustrated in FIG. 8, in a case where a mechanism for picking up and elevating the T tip 7 approaches the T tip 7, the circular magnetic plate is attached to a magnet disposed under the mechanism such that the pick-up can be easily performed.

Hereinafter, a process of proceeding immunoassay by using the cartridge system 1 will be described in more detail.

An immunoassay method according to another embodiment of the present invention may be performed in the following process.

Figure 9:
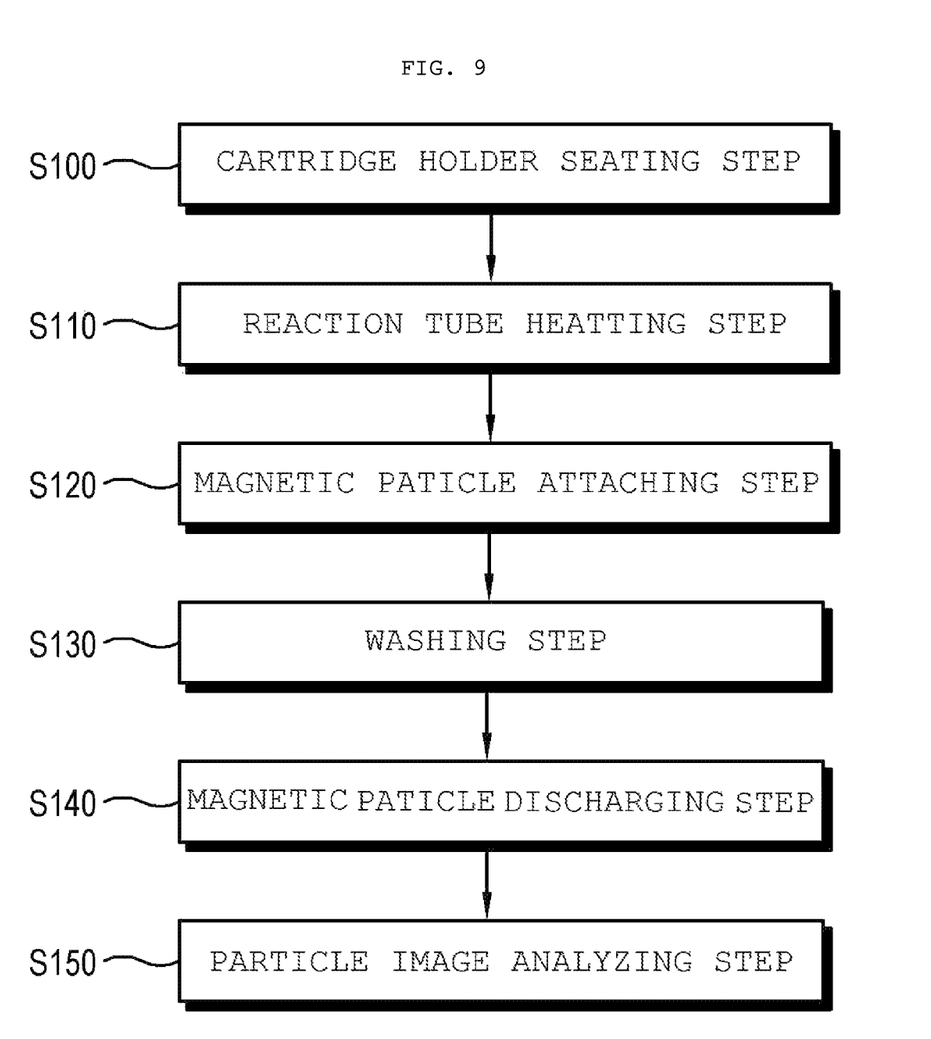
FIG. 9 is a flowchart illustrating a process of proceeding an automatic immunoassay method of the present invention.

As illustrated in FIG. 9, the present invention includes a first step S100 of injecting a certain amount of a sample into the reaction tube 11 of the cartridge 13, inserting the T tip 7 into the tube for T tip 9, and then seating the cartridge 13 in the cartridge holder 15; a second step S110 of proceeding the reaction by heating the reaction tube 11 to generate a predetermined temperature by applying power to the heating member 17; a third step S120 of inserting the T tip 7 into the reaction tube 11 by the pick-up machine 40, and attaching the magnetic particles m on the outer surface of the T tip 7 due to the magnetic force of the magnet rod 31 after proceeding the reaction; a fourth step S130 of performing washing by up and down reciprocating movement after moving to the washing tube in a state where the magnetic particles m are attached to the outside of the T tip 7; and a fifth step S140 of discharging the magnetic particles m to the tube for signal measurement 5 by raising the magnetic rod 31 from the T tip 7 after moving the T tip 7 to the tube for signal measurement 5.

The immunoassay method will be described in detail.

Figure 4A:
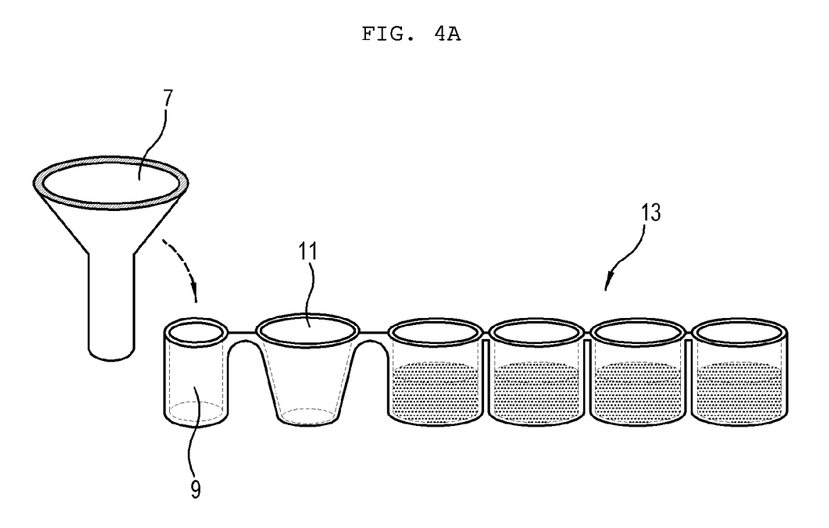
FIG. 4a is a diagram illustrating a process of inserting the T tip illustrated in FIG. 1 into the tube for T tip.

As illustrated in FIG. 4*a*, first, in the first step S100, after a certain amount of a sample is injected into the reaction tube 11, the T tip 7 is inserted into the tube for T tip 9. In this state, the cartridge 13 is seated in the cartridge holder 15.

As the second step S110, the reaction tube 11 is heated by applying the power to the heating member 17 to generate a predetermined temperature.

If the reaction tube 11 is heated by the predetermined temperature, the reaction proceeds.

Figure 4B:
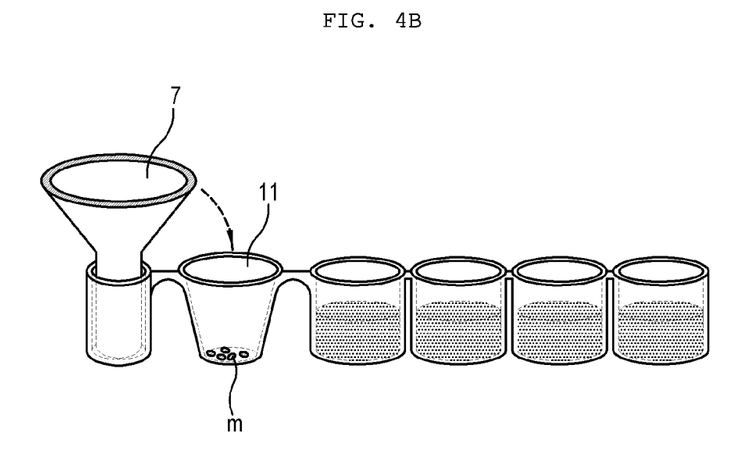
FIG. 4b is a diagram illustrating a process of moving the T tip to and inserting into the reaction tube.
Figure 5:
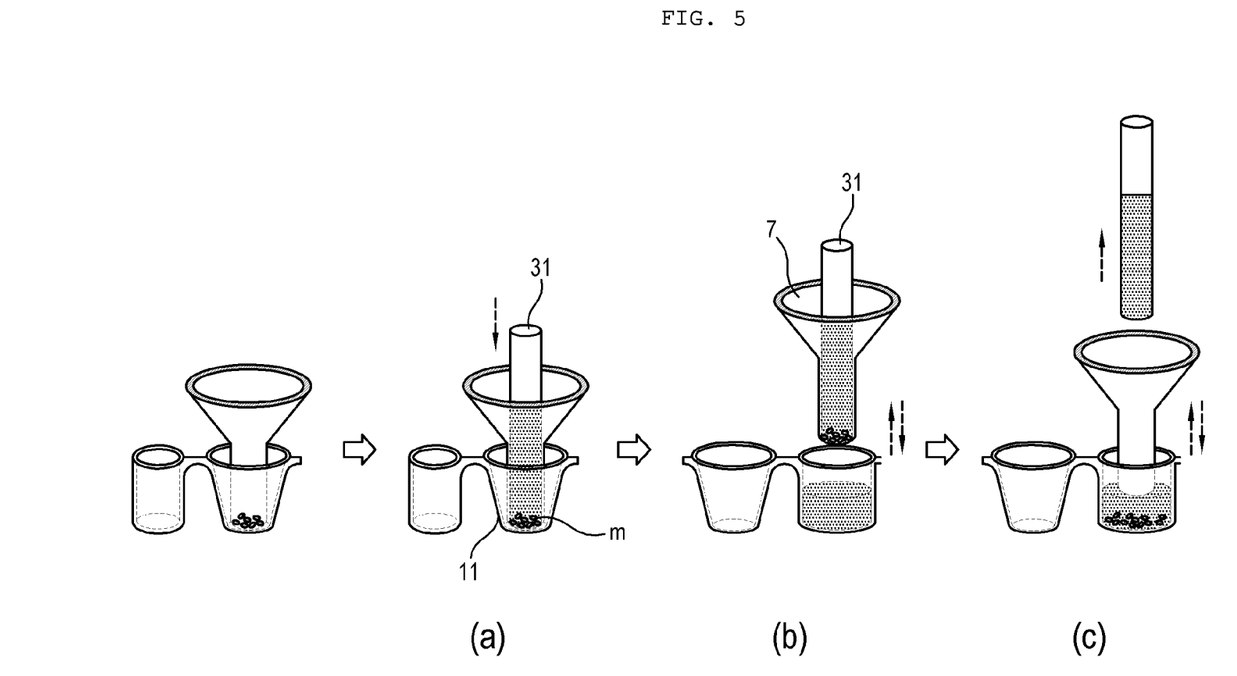
FIG. 5a illustrates a process of attaching large magnetic particle composites of various shapes in the reaction tube by descending a magnetic rod after the T tip illustrated in FIG. 1 is inserted into the reaction tube.
FIG. 5b illustrates a process of moving up and down the magnetic rod and the T tip together after moving them to a first tube for washing while the magnetic rod is inserted into the T tip.
FIG. 5c is a diagram illustrating that only the T tip is moved up and down after the magnetic rod is separated from the T tip.
Figure 6:
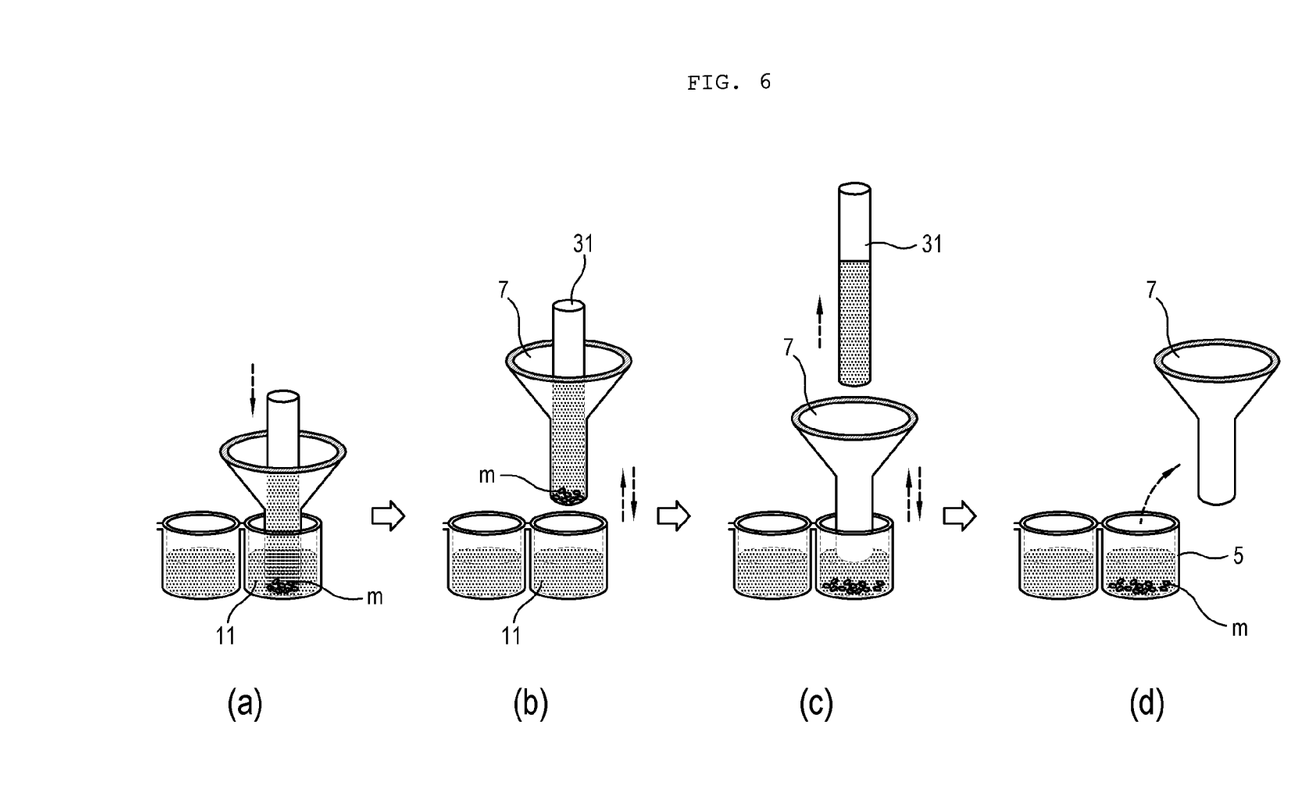
FIG. 6a illustrates that the T tip inserted into the magnetic rod is moved from the first tube for washing to a second tube for washing.
FIG. 6b illustrates a process of washing the large magnetic particle composites of various shapes while the T tip is moved up and down in the second tube for washing.
FIG. 6c illustrates a process of washing the large magnetic particle composites of various shapes while only the T tip is moved up and down after separating the magnetic rod from the T tip.
FIG. 6d illustrates a process of putting down the large magnetic particle composites of various shapes by entering the T tip in the tube for signal measurement, and removing the T tip.

After proceeding the reaction, as illustrated in FIG. 4*b*, as the third step S120, the T tip 7 is moved to and inserted into the reaction tube 11 by the pick-up machine 40.

As illustrated in FIG. 5*a*, if the T tip 7 enters the inside of the reaction tube 11, the magnetic rod 31 is lowered to reach the inner bottom of the reaction tube 11.

A magnetic field is formed by the magnetic rod 31 within an outer predetermined radius of the T tip 7 so that the magnetic particles m stored in the reaction tube 11 are attached to the outer surface of the T tip 7. At this time, the magnetic particles are in a state where a material (for example, antibody) capable of capturing the analyte material is basically bound thereto and configured with the magnetic particles of one shape or various shapes.

Therefore, since it is configured that each of the different shapes of magnetic particles is bound with materials (for example, antibody) capable of capturing only specific analyte materials, if the analyte materials are present in a sample, the analyte materials are captured in the magnetic particles and the signal materials (for example, another antibody with fluorescent material) are bound with the analyte materials captured in the magnetic particles such that the magnetic material-analyte material-signal material composites are formed. After the reaction, a magnetic composite, sample impurity that does not react with the magnetic material, and a signal material remaining without the reaction are present together in the reaction tube.

As described in FIG. 5*b*, in a state where the magnetic particles m and the magnetic particle composite are attached to the T tip 7, as the fourth step S130, the T tip 7 moves the first tube for washing and performs up and down reciprocating movement while being inserted into the magnetic rod 31.

As described above, by separating a foreign material from materials attached to the outer surface of the T tip 7 by up and down reciprocating movement, washing is performed in the washing tube 3 (FIG. 5*c*).

As described in FIG. 6*a*, the T tip 7 in a state where the magnetic particles m and the magnetic particle composite are attached to the outer thereof, is moved to the second tube for washing, and then enters the second washing tube.

As described in FIG. 6*b* and FIG. 6*c*, while the T tip 7 moves up and down to wash the magnetic particles m and the magnetic particle composite a second time.

That is, by elevating the lower portion by the pick-up machine 40 in a state where the lower portion of the T tip 7 is immersed in cleaning liquid of the cleaning tube (at this time, state where magnetic particles are attached on outer of T tip), foreign materials other than the magnetic particles m attached on the outer surface of the T tip 7 may be separated.

That is, the signal materials randomly attached to the T tip are cleaned from the magnetic particles m and the magnetic particle composite attached to the outer surface of the T tip 7 without reacting with the impurities present in the sample.

This process may be repeated in each of the tubes for washing 3 equally, and thus the T tip 7 may be effectively cleaned by repeating the washing process many times.

After the cleaning process of the T tip 7 is completed in the last cleaning tube, as described in FIG. 6*d*, as the fifth step S140, after moving to the tube for signal measurement 5, the magnetic particles m and the magnetic particle composite are discharged to the tube for signal measurement 5 by raising the magnetic rod 31 from the T tip 7.

In addition, a sixth step S150 may be further included. In this step, the multiple inspections may be performed simultaneously by capturing and separating only specific analyte materials per the magnetic particles of one shape or various shapes by analyzing the discharged large magnetic particles m as images by the image analyzer (14; FIG. 1).

That is, as described in FIG. 7, the magnetic particles m and the magnetic particle composite discharged and sunk to the tube for signal measurement 5 may be distinguished in shape by using the image analyzer (14; FIG. 1) according to the shapes.

That is, since each shape may be recognized as a result of different materials by analyzing and imaging a shape of the large magnetic particles with the image analyzer 14, multiple scanning may be performed simultaneously in one tube.

An automatic immunoassay process may be performed through the above processes.

INDUSTRIAL AVAILABILITY

The present invention relates to an immunoassay apparatus and a method thereof, more specifically, and is available in a field of immunological research, as a technology in which a washing process, is automatically performed in one cartridge, of increasing the accuracy of immune response results by using a structure of a magnetic rod and a T tip used for extracting and discharging the large magnetic particles of various shapes by using a simple method, and using the large magnetic particles, by improving a structure.

The invention claimed is:

1. A cartridge system of an immunoassay apparatus comprising:
   a cartridge in which a tube for a T tip, a reaction tube, a plurality of washing tubes, and a signal measurement tube are integrally coupled or individually configured;
   a T tip and a magnetic rod configured to perform reaction and washing processes while moving large magnetic particles of various shapes, capture materials, signal materials, and analyte materials with magnetic force by entering successively the plurality of washing tubes and the signal measurement tube;
   a cartridge holder in which the cartridge is seated;
   a heating member that generates heat by being disposed at a region in which the reaction tube is seated in the cartridge holder; and
   an image analyzer configured to perform multiple inspections by recognizing each of the analyte materials bound to the magnetic particles by analyzing the magnetic particles of various shapes as images,
   wherein the cartridge holder includes:
      a first mounting stage in which the tube for the T tip is seated;
      the heating member in which the reaction tube is seated and heated;
      a second mounting stage in which the plurality of washing tubes are seated; and
      a third mounting stage in which the signal measurement tube is seated, and
   wherein a first distance between the reaction tube and the tube for the T tip and a second distance between the reaction tube and the plurality of washing tubes are maintained longer than a thickness of the heating member.

2. The cartridge system of the immunoassay apparatus according to claim 1,
   wherein the T tip includes
      a pipe body that is disposed in a lower portion and magnetic particles attached to an outer surface, and
      an induction pipe of an inverted triangle is disposed in an upper portion of the pipe body,
   wherein the magnetic rod can move up and down through the induction pipe and the pipe body.

3. The cartridge system of the immunoassay apparatus according to claim 2,
   wherein a magnetic plate is disposed on an upper edge of the induction pipe of the T tip to be able to attach to a pick-up machine.

4. An immunoassay method comprising:
   a first step of injecting a predetermined amount of a sample into a reaction tube of a cartridge, inserting a T tip into a tube for a T tip, and then seating the cartridge in a cartridge holder;
   a second step of proceeding reaction by heating the reaction tube to generate predetermined temperature by applying power to a heating member;
   a third step of inserting the T tip into the reaction tube by a pick-up machine, and attaching magnetic particles having various shapes on an outer surface of the T tip due to magnetic force of a magnet rod, after proceeding the reaction;
   a fourth step of performing washing by up and down reciprocating movement after moving to a washing tube in a state where the magnetic particles are attached to outside of the T tip;
   a fifth step of discharging the magnetic particles to a signal measurement tube by raising the magnetic rod from the T tip after moving the T tip to the signal measurement tube; and
   a sixth step of capturing and separating only specific analyte materials bound to the magnetic particles of one shape or various shapes by analyzing the discharged large magnetic particles as images by an image analyzer,
   wherein the cartridge holder includes:
      a first mounting stage in which the tube for the T tip is seated;
      the heating member in which the reaction tube is seated and heated;
      a second mounting stage in which the plurality of washing tubes are seated; and
      a third mounting stage in which the signal measurement tube is seated, and
   wherein a first distance between the reaction tube and the tube for the T tip and a second distance between the reaction tube and the plurality of washing tubes are maintained longer than a thickness of the heating member.

5. The immunoassay method according to claim 4,
   wherein in the fourth step, a washing process proceeds, of separating foreign materials other than the magnetic particles attached on the outer surface of the T tip by elevating the T tip by the pick-up machine in a state where the lower portion of the T tip is immersed in cleaning liquid of a cleaning tube.

* * * * *